United States Patent [19]

Parker

[11] Patent Number: 5,419,870

[45] Date of Patent: * May 30, 1995

[54] ANTIBODY TESTING SYSTEM

[75] Inventor: James E. Parker, Long Beach, Calif.

[73] Assignee: V-Tech, Inc., Pomona, Calif.

[ * ] Notice: The portion of the term of this patent subsequent to Jan. 10, 2006 has been disclaimed.

[21] Appl. No.: 979,841

[22] Filed: Nov. 23, 1992

Related U.S. Application Data

[63] Continuation of Ser. No. 695,950, May 6, 1991, abandoned, which is a continuation-in-part of Ser. No. 6,874, Jan. 27, 1987, Pat. No. 4,797,260, which is a continuation of Ser. No. 229,455, Aug. 8, 1988, abandoned.

[51] Int. Cl.$^6$ ............................................. G01N 33/53
[52] U.S. Cl. ................................. 422/56; 422/57; 422/58; 422/101; 435/7.1; 435/301; 435/805
[58] Field of Search ....................... 472/55–58, 472/69, 100–104; 435/7.1, 301, 805

[56] References Cited

U.S. PATENT DOCUMENTS

| | | | |
|---|---|---|---|
| 4,789,526 | 12/1988 | Matkovich | 422/101 |
| 4,797,259 | 1/1989 | Matkovich et al. | 435/7 |
| 4,797,260 | 1/1989 | Parker | 422/101 |
| 4,874,691 | 10/1989 | Chandler | 422/101 |
| 4,908,319 | 3/1990 | Smyczek et al. | 422/103 |

Primary Examiner—Timothy M. McMahon
Attorney, Agent, or Firm—Drucker & Sommers

[57] ABSTRACT

A device for performance of ligand-receptor assay methods for determining the presence of a liquid. The preferred ligand-receptor pair are antigen-antibody pairs. The device has a membrane having the receptor physically bound to its surface. The membrane is disposed at the top of a body member, and is affixed thereto by means for attaching, which is preferably a cap with a funnel depression. A porous means is disposed below the membrane to absorb liquid. Substantially all of the top surface of the membrane is exposed. The receptor site typically occupies only a portion of the top of the membrane, and in a preferred embodiment, a funnel member releasably attaches to the cap, thereby conveying the sample through only that area of the membrane having the receptor site. The device has a piston means disposed inside the body member, and in air-tight seal with the body member. Means to actuate the piston means are disposed outside the body member. The piston means creates a region of reduced pressure to urge the sample through the membrane.

8 Claims, 3 Drawing Sheets

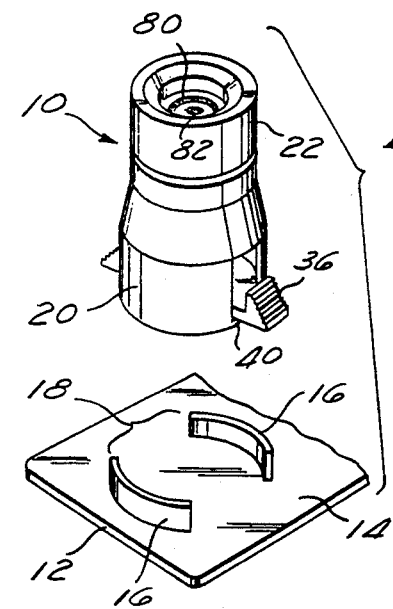
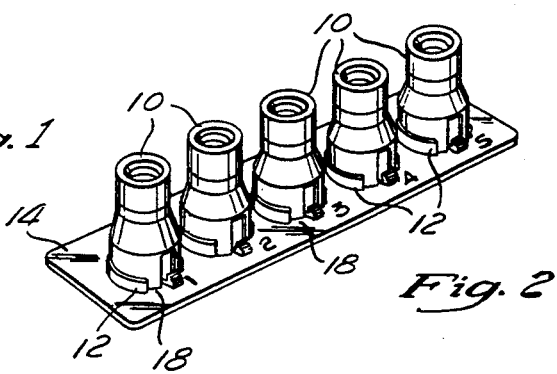
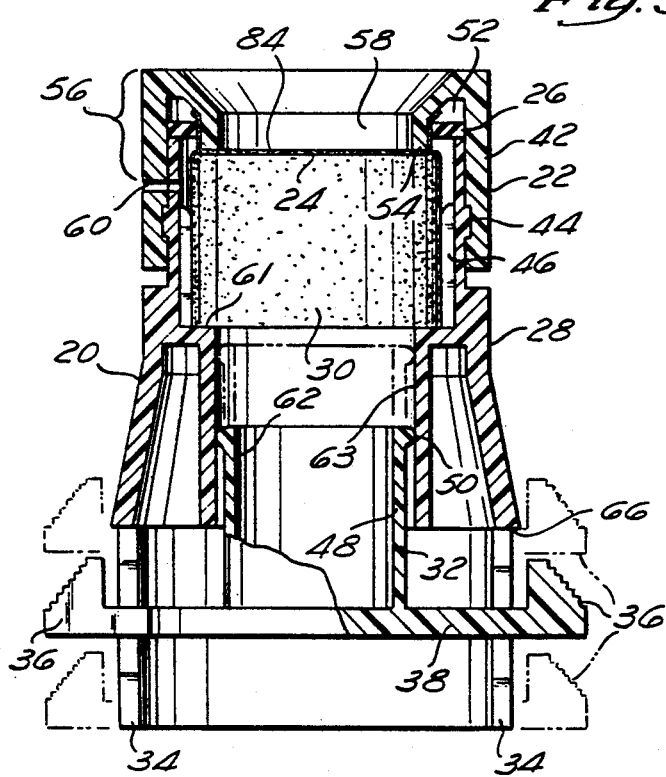
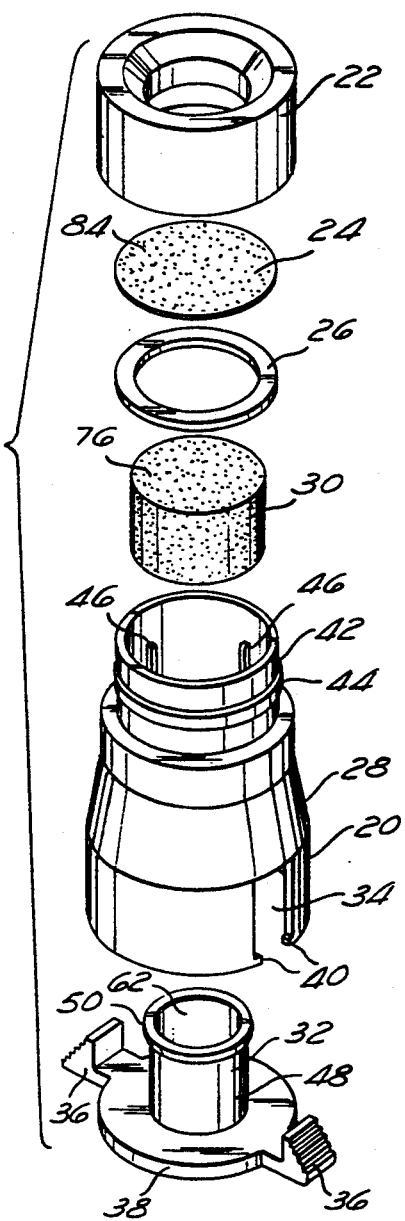
Fig. 1
Fig. 2
Fig. 3
Fig. 4

ANTIBODY TESTING SYSTEM

This application is a continuation of U.S. patent application Ser. No. 07/695,950, filed May 6, 1991, now abandoned, which is a continuation-in-part of U.S. patent application Ser. No. 07/006,874, filed Jan. 27, 1987, now U.S. Pat. No. 4,797,260, issued Jan. 10, 1989, which is a continuation of Ser. No. 229,455, filed Aug. 8, 1988, now abandoned.

BACKGROUND OF THE INVENTION

1. Field of the Invention

This invention relates to apparatus and methods for testing for the presence of antigens using antibodies.

2. Prior Art

There are a variety of apparatuses designed to ease immuno testing.

Valkirs et al. disclose in U.S. Pat. No. 4,727,019 a device having a body member that contains a porous mass. A membrane having a ligand-receptor is disposed above the porous mass. The sample solution flows into the porous mass by capillary action only. There is no teaching of any means to reduce pressure to facilitate more rapid liquid transfer.

In U.S. Pat. No. 4,090,850 issued to Chan, an antibody coated cellulose paper is used in radioimmunoassays in conjunction with the test apparatus comprising a receptacle tray with multiple wells. Each of said wells having at its bottom an orifice such that the multiple wells can be simultaneously evacuated by a single source of reduced pressure.

In U.S. Pat. No. 3,888,629 issued to Bagshawe, a reaction cell for the performance of radioimmunoassay determinations and the like is disclosed. Here two halves of the cell are joined together, separated by a membrane containing the necessary antibodies to form a particulate reaction product. The liquid reagents flow through the membrane under the influence of gravity.

U.S. Pat. No. 4,424,279 issued to Bohn discloses an immunoassay apparatus having a cylindrical tube that has a plunger filter assembly slideably fitted therein. The filter is dome shaped and contains beads sensitized with immunologically reactive material.

Greenspan U.S. Pat. No. 4,189,385 discloses a method and apparatus for separating serum or plasma from the formed elements of blood. The apparatus disclosed is generally similar to that of Bohn, except instead of a filter, a one way valve is disclosed.

In Buono U.S. Pat. No. 4,057,499, another apparatus for the separation of blood is taught. The apparatus is similar to the apparatus disclosed in Bohn and Greenspan. The one way valve of Greenspan is a filter, but unlike the filter in Bohn, it contains no immunologically reactive material.

Moore et al. U.S. Pat. No. 3,870,639 teaches yet another similar blood plasma separation device. Other filtration devices include U.S. Pat. No. 4,522,713 to Nussbaumer and U.S. Pat. No. 3,687,246 to Spinosa.

Bohn, Greenspan, and Buono rely on a slight pressure differential being created when a plunger portion is forced into contact with fluid contained in an outer tube. The fluid beneath the plunger filter or valve is then forced upwardly into a receiver tube fitted within the outer tube.

A problem with prior testing devices is that an analytical laboratory, complete with vacuum lines is required to use the devices. It would be advantageous to have a device that requires no external source of vacuum. The present invention provides an externally manipulable piston for creating a region of reduced air pressure beneath a membrane binding an analytic compound, preferably an antibody. The region of reduced pressure causes the fluid to be tested to be rapidly drawn through the membrane.

Another problem with prior art devices has been that much of the sample never contacts the receptor site. Tests with increased sensitivity would result if all the sample contacted the receptor region.

Another problem is that the sample frequently does not contact the receptor site for sufficient time for a liquid receptor complex to form. It would be advantageous to provide an embodiment whereby the membrane that supports the receptor is not initially in contact with the liquid absorbing porous means.

SUMMARY OF THE INVENTION

This invention provides a device for the performance of ligand-receptor assay methods for determining the presence of a ligand. The device has a membrane having the receptor physically bound to its surface. The membrane is disposed at the top of a body member, and is affixed thereto by a means for attaching, which is preferably a cap with a funnel depression. A porous means is disposed below the membrane to absorb liquid. Substantially all of the top surface of the membrane is exposed. The receptor site occupies a portion of the top surface of the membrane. In a preferred embodiment a funnel member releasably attached to the cap, thereby conveying the sample through only that area of the membrane having the receptor site. The device has a piston means disposed inside and in air-tight seal with the body member. The piston creates a region of reduced pressure to urge the sample through the membrane.

An aspect of this invention is a device for ligand-receptor assay processes for determining the presence of a ligand comprising:
  a body member;
  a membrane having a top an a bottom surface disposed on the top of said body and having a receptor bound to a portion of the membrane;
  means for attaching said membrane to the body member that provides access to substantially the entire top surface of the membrane;
  means for receiving liquid disposed below the membrane within the body member; and
  piston means for creating a region of lesser pressure disposed below the means for receiving.

BRIEF DESCRIPTION OF THE DRAWINGS

FIG. 1 is perspective view an embodiment of this invention, together with a preferred mounting means.

FIG. 2 is a perspective view of a plurality of mounted testing units.

FIG. 3 is an exploded perspective view of an embodiment of this invention.

FIG. 4 is sectional view of an embodiment of this invention.

DETAILED DESCRIPTION OF THE INVENTION

Figure 5:
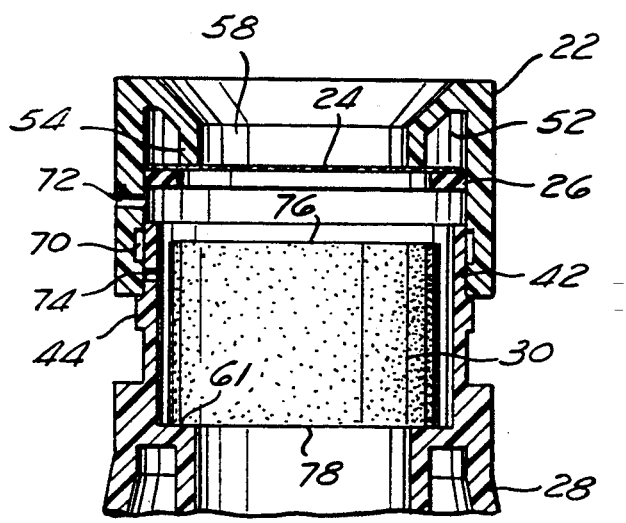
FIG. 5 is a sectional view of the embodiment of FIG. 2 prior to snap fitting the cap to the body member.

As used herein the word "ligand" is a compound or biological material whose presence is being determined. Examples include small molecules, such as cocaine, morphine, or progesterone; medium molecules, such as LHRH; large molecules, such as DNA, or LCG; and ether biological materials, such as bacterial cell walls, viruses and the like.

As used herein, the word "receptor" is a compound or biological material that binds to a ligand. Preferred receptors are antibodies, including both polyclonal and monoclonal antibodies. The term also includes the active portion, or FAB fragment of antibodies, if it has been cleaned from the rest of the molecules.

As used herein the term "sample solution" is a solution that is suspected of containing a particular ligand. It is realized that a sample solution will frequently contain no ligand, or, in other words, the test for that ligand is negative.

Referring to FIG. 1, the assembled antibody testing unit 10 can be placed onto a mounting means 12. A surface plate 14 has retaining walls 16 that have a handle relief 18 that allows the piston handle to be depressed to the surface plate. The fit of the retaining walls with the base of the unit 20 should be snug enough so that the unit does not wobble when used.

Referring to FIG. 2, a plurality of assembled testing units 10 are received by a plurality of mounting means. Then a series of tests can be run simultaneously. The series can be either several different tests for one individual or the same test for several individuals.

Referring to FIG. 3, a cap 22 receives membrane 24 which supports the receptor to the ligand and a membrane retaining ring 26. Both the cap and the retaining ring are preferably made of molded plastic, although other materials known in the art will work as well. The membrane is made of material known to bind the receptors. It is preferred that the component be an antibody and the material bind proteins. Examples of such material include: nitrocellulose; Pall biodyne, which is a chemically activated nylon; and the like. The membrane retaining ring is of a dimension to snugly fit within the cap and not move once it is positioned in the cap.

A body member 28 receives porous filter member 30. The porous filter member is made of hydrophilic material. The body member is preferably made of the same material as the cap, preferably molded plastic. The body member has a base member 20 that extends upwardly and slopes inwardly. The base member terminates and a body extension 42 extends upwardly. A snap fit ring 44 encircles the body extension. Porous filter retaining members 46 disposed inside the body extension secure and center the porous filter member.

A piston member 32 is disposed in the body member below the porous filter member 61. Piston walls 48 extend upwardly from the piston base plate 38, and terminate in a periferal lip 50 that sealingly engages the piston housing when assembled. The sides of the body member contain two oppositely disposed slots 34 disposed in the base of the body member 20 to receive piston handles 36 that extend from the piston base plate and allow longitudinal movement of the piston handles. At the base of the slot is a handle retaining extension 40 to prevent the piston from accidentally disengaging from the body member when the piston is fully depressed.

The cap 22, including the membrane 24 and the retaining ring 26, is snap fit to the body member 28 which includes the porous filter member 30 and the piston 32. This assembly forms the final immunoassay unit 10. The cap, when snap fit to the body, will preferably be rotatable.

Referring now to FIG. 4, the cap member 22 is mated to the body member 28 by engaging the snap fit ring 44, which encircles the body extension 42. The ring is disposed within a snap fit relief, which encircles the cap.

A relief 52 in the cap member 28 receives the retaining ring. The membrane 24 is securely positioned within the relief between the retaining ring and the cap. A membrane engagement lip 54 on the cap forces the membrane into intimate contact with the entire surface of the porous filter member 30. The membrane retaining ring rests on the body extension 42, which forces the membrane retaining ring as far into the cap relief as possible. The membrane is secured in the cap relief by the membrane retaining ring and snugly covers the tap surface of the porous filter member.

When the membrane contacts the porous filter member, fluid is drawn through the membrane by adsorption. An upward extension of the cap 56 allows a depression 58 to be formed for receiving the sample solution. A volume of sample solution can be placed in the depression. At the bottom of the depression is the top of the membrane 60. The top of the membrane has been impregnated with an antibody. This antibody will react with the antigen being tested for.

The porous filter member 30 is supported on an internal support 61. The porous filter member is disposed above a piston housing 63 and is in vacuum communication with the piston housing. That is, if the piston is depressed, creating a zone of reduced air pressure acts directly on the bottom surface of the porous filter. Within the piston housing, the piston member 32 is sealingly engaged with the walls of the piston housing by a sealing means. Preferably, the top of the circumferential wall terminates in a peripheral lip 50 extending outwardly, which engages the walls of the piston housing as the sealing means. In a preferred embodiment the piston has a piston wall 42 forming a central well 44. The central well can accumulate liquid reagents or washing fluids used during the test for the ligand. Piston handles 36 attached to the piston base plate 38 extend through a slot 34 allowing manipulation of the piston. The piston handles are oppositely disposed on the piston base plate. The piston is shown depressed about half way, but the piston can be depressed all the way to the bottom of the body member 64 and can be raised to the piston handle stop 66 as shown in phantom.

When the piston handles 36 are externally manipulated, usually by a lab technician performing the test, but possibly by automatic means, the piston moves downwardly to the lower position forming a region of reduced air pressure. Then, the fluid to be tested is rapidly drawn through the membrane.

In a preferred embodiment, the cap 22 and the body member 28 have vacuum release aperature 60 that extends from the exterior of the cap member through the body member to the atmosphere. The user of the unit can create an area of low pressure by rotating the cap thereby disaligning the hole in the cap and the hole in the body member. Alternatively, the user can leave the holes aligned, thereby preventing the piston from creating a low pressure region.

The porous filter member is a fluid removing means that intimately contacts the membrane. Fluid is drawn through the membrane, by the fluid removing means. The piston can act as an air pressure reduction means to rapidly draw fluid through the fluid removing means. The liquid reagents and washing fluids can be removed from contact with the membrane by the fluid removing means. If the fluid removing means is prevented from removing fluid, perhaps because it is saturated, the air pressure reduction means can draw excess fluid from the fluid removing means. The air pressure reduction means is in vacuume communication with the fluid removing means. The air pressure reduction means speeds tests conducted in the apparatus because there is no waiting for fluids filling the depression 18 or saturating the fluid removing means to drain by gravity.

Referring to FIG. 5, the cap 22 is shown as it would be in relation to the body 28 immediately before downward pressure is applied to snap fit the cap and body member. The membrane 24 is retained in the cap by the retaining ring 26, which is held into place by friction.

A snap fit relief 70 can receive the snap fit ring 44 when downward pressure is applied. Both the cap and the body must be made of resilient material, preferably molded plastic, to prevent breakage of either piece in this operation. The vacuum release aperature in the cap 72 will align with the vacuum release aperature in the body member 74.

The porous filter member 30 has a flat top surface 76 and a flat bottom surface 78. The porous filter member is retained by the internal support 61. The porous filter is disposed above the piston housing 63. When the cap is snap fit onto the body member, the body member extension 42 engages the retaining ring 26 and forces it into the relief in the cap 52, thereby deforming the membrane and stretching it tightly across the top surface of the porous filter member. The membrane engagement lip forces the membrane downwardly into the porous filter member creating a relief along the circumference of the top surface of the porous filter member. In this way, intimate contact of the entire surface of the membrane with the top surface of the porous filter member is assured, that is, the membrane covers and contacts all points of the top of the porous filter member. It is preferred that the top surface of the porous filter member be flat, but since the filter material can be easily deformed, a slightly convex top surface is preferably employed.

It is preferred that the body member, the cap and the piston all be made of moldable plastic. Such construction provides low cost components that are easily assembled. The outward extension of the piston wall has superior wall engagement properties when made of molded plastic. The porous filter member can be made of any hydrophillic adsorbant, for example, filter paper.

Figure 6:
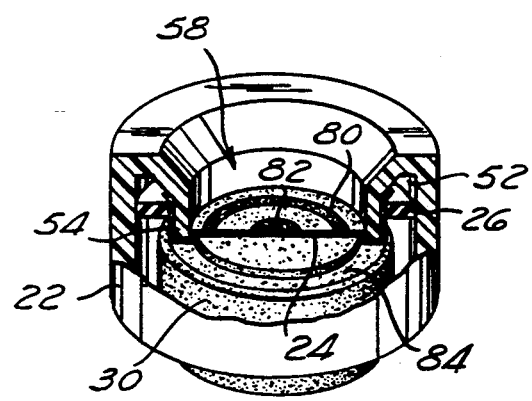
FIG. 6 is a partially cut away perspective view of the cap of this invention.

Referring to FIG. 6 the membrane 24 is forced into contact with the porous filter 30 by the membrane engagement lip 54. This deforms the porous filter forming a circular depression 84. The edge of the membrane is retained by the retaining ring 26 in the relief in the cap 52. The top surface of the membrane forms the bottom of the depression 58. The antibodies used in the test impregnate the top surface of the membrane. If two antibodies are used they can form a pattern, in the case shown, a ring 80 and a central dot 82. It will be appreciated that normally the unreacted pattern is invisible, and that only a positive test results in the entire pattern being visible.

As shown, the retaining ring is forced as deeply into the recess 56 as possible, and is kept there by the body member extension. The body is not shown in this drawing, but the cap having the deformed porous filter is snap fitted to the body.

Figure 7:
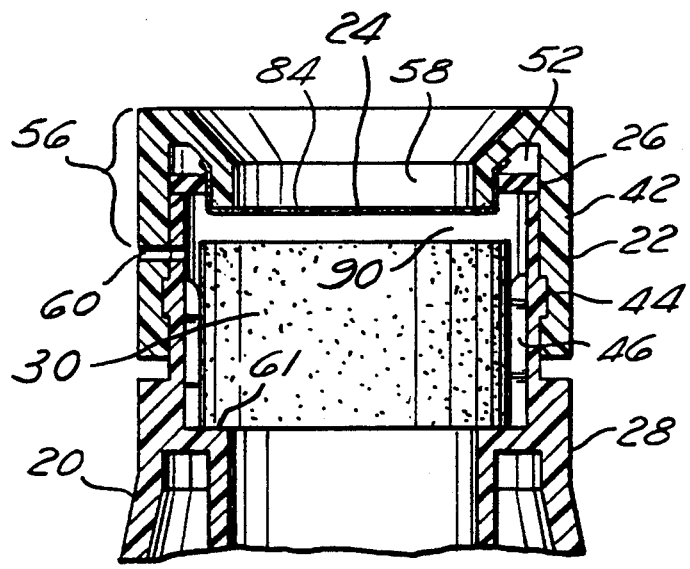
FIG. 7 is a cut away of an alternative embodiment.

Referring to FIG. 7, the porous member is disposed so that an air gap 90 exists between the membrane 24 and the porous member 30. The membrane has the receptor impregnated on its surface. In operation of the device, the sample solution is placed on the membrane surface. Then the external handles are manipulated, thereby forming a region of reduced pressure that draws the excess liquid through the membrane.

The membrane is flexible, and therefore can be made to meet the porous member if the air gap is made small enough. This establishes capillary action to aid in removing excess liquid. One advantage of the configuration of FIG. 7 is that slowly reacting components, one in the sample solution and one on the membrane, can remain in contact for the full length of time required to react.

The porous member may be friction fitted to prevent movement inside the receiving cavity, although this is not a requirement. If the porous member is movable, capillary attraction may be established by tilting the apparatus upside down and allowing the porous member to contact the membrane.

Figure 8:
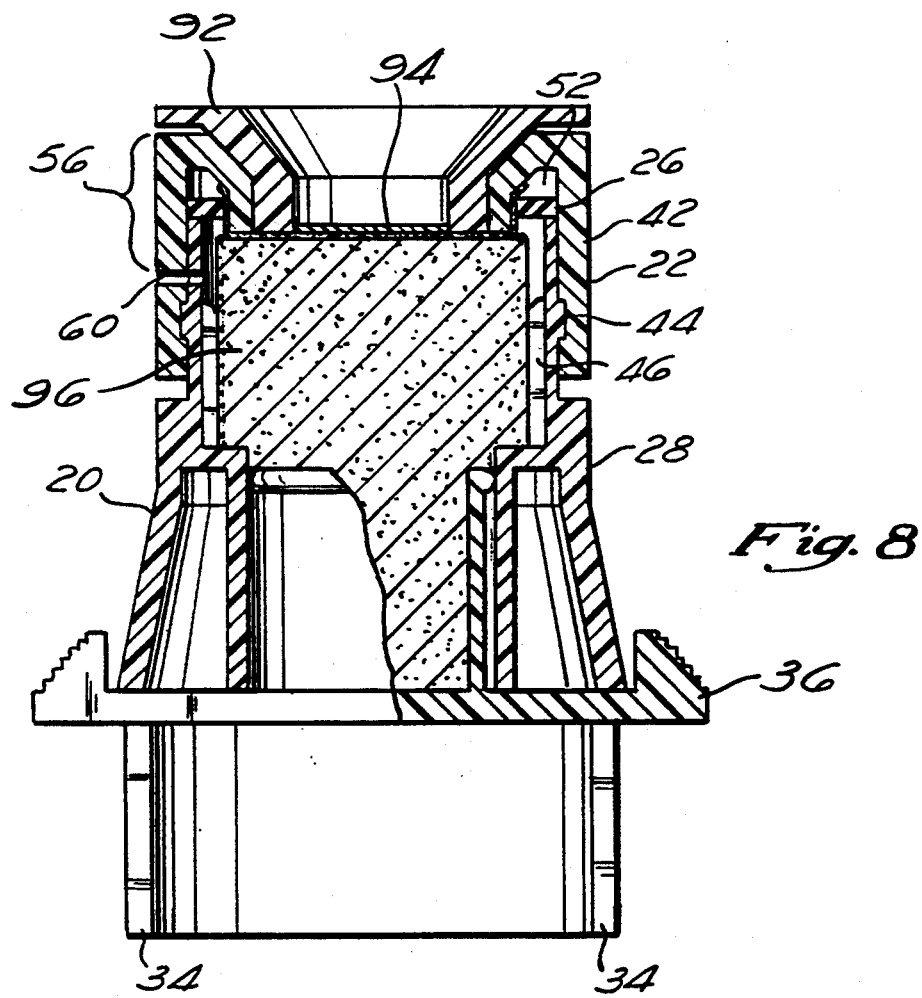
FIG. 8 is a perspective partially cut away view of the cap of FIG. 6 with a separatable funnel member.

Referring to FIG. 8, the cap 22 is shown fitted with a separatable sample concentrator funnel member 92. The funnel member snugly friction fits within the depression formed by the cap walls.

The sample concentrator funnel allows the sample solution to pass only through the receptor site on the membrane. The analyte in the sample has a greater chance of reacting with the receptor site if all the sample solution passes through the receptor site, thereby significantly enhancing the sensitivity of the test.

The sample concentrator funnel sits snugly within the funnel of the top of the body member. The fit can be enhanced with engagement members formed when a plastic cap is formed. It is preferable, but not mandatory, that a filter member cover the bottom of the sample concentrator funnel. Then more contaminated samples, such as essentially untreated biological samples, can be run through the test apparatus. Examples of such fluids include blood serum, urine, and the like.

The sample essentially all contacts the receptor site which covers the exit from the concentrator funnel. After the sample has contacted the active zone, the sample concentrator funnel is removed and a test verification sample contacts the entire surface of the membrane. The test verification ring does not need the increased sensitivity provided by the sample concentrator funnel.

Other methods of increasing the sensitivity of the test include increasing the time of contact between the membrane and the sample. One can achieve this goal by placing a hydrophobic barrier between the membrane and the liquid retainer. Alternatively, one can allow the liquid to sit on the membrane for a period of time before activating the plunger.

The porous member is granular desiccant 96. Examples of suitable desiccants include silica gel, calcium, chloride and the like. During manufacture, the desiccant is packed into the body member having the vacuum plunger in the up position. The desiccant will absorb water from the reagents placed on the membrane. When needed the plunger is moved downwardly, urging the reagents through the membrane. Although the desiccant is shown extending to the bottom of the piston member, it need not extend that far. Nor need the top level of the desiccant abut the membrane. An air gap can be provided.

When the embodiments as shown in FIGS. 4 and 7 are shipped from the factory, packets of dessicant are added to the packaging of the devices. This is to keep the reagents and reactants bound to the membranes as fresh as possible. One advantage to the use of desiccant as absorbant material as shown in FIG. 8 is that no extra packets of desiccant need to be added to the shipping package.

In use, the unit is mounted on a mounting means. The membrane will have been impregnated with a receptor to a ligand that is to be tested for. For example, in a pregnancy test, the membrane will have been impregnated with anti-hCG. The sample solution can be either a urine sample or a blood serum sample. After the fluid has been contacted with the membrane and withdrawn into porous filter member, a second labeled antibody is contacted with the membrane. If the ligand is present, it will be bound to the first receptor on the surface of the membrane. The bound ligand then acts as a receptor and binds a second, labeled receptor. This is sometimes referred to in the art as a "forward sandwich" assay. See for example, U.S. Pat. No. 4,376,110 issued David et al. If the antigen is present, then the label will be present on the surface of the membrane. The label can be a radiometric, a fluormetric label, and enzymatic label, a colorometric label, or any of a number of other labels well known in the art. It will be appreciated that the present invention is not limited to sandwich assays, but is general for other heterogeneous assays known in the art.

One advantage of the device of the present invention is that tests can be run on a wide variety of compounds in fluids. For example, if the pH of water is to be tested in the device of the present invention, the membrane could be litmus paper. Other similar non-antibody tests will immediately suggest themselves to the skilled artisan. Of course, the preferred tests are antibody tests. The device of the present invention can facilitate tests for a wide range of antigens. A great advantage of the device is that different fluids can be tested for. For example, blood serum and urine can both be tested in the same unit.

Of course, almost any antigen can be analyzed for using the apparatus of the present invention. For example, one can test for hGC, for viral infections such as AIDS or herpes, drugs of abuse such as cocaine or heroin, difficult to diagnose bacterial diseases such as chlamydia or asymptomatic gonorehea, and other antigens.

In a preferred embodiment, at least two different antibodies are present on the membrane, for example, anti-LCG and anti-horseradish peroxidase. The first antibody tests for the presence of the antigen. The second can test if the reagents are working properly, that is, it should always be a positive test if the reagents are added in the correct order. When colorometric labels are used, the two antibodies can be placed on the membrane to form a pattern. For example, a minus if the test is negative, or a plus if the test is positive, or a ring and an inner dot forming a bullseye if the test is positive, and a ring if the test is negative. The membrane is impregnated using the apparatus of U.S. Pat. No. 4,748,042.

The embodiments described are the currently preferred embodiments, but the scope of the invention should not be considered limited by anything other than the appended claims.

I claim:

1. A device for ligand-receptor assay processes for determining the presence of a ligand comprising a body member;
   a membrane having a top surface and a bottom surface disposed on the top of said body member having receptor bound to a portion of the membrane;
   means for attaching said membrane to the body member that provides external access to substantially the entire top surface of the membrane;
   a porous granular liquid absorbent mass for receiving liquid disposed below and having direct access to allow contact with substantially the entire bottom surface of the membrane within the body member; and
   piston means for creating a region of lesser pressure disposed below the means for receiving.

2. The device of claim 1, wherein said porous member and said membrane define a space therebetween.

3. The device of claim 1 wherein said means for allowing fluid to flow into contact which said membrane is a cap means overlying said membrane, said cap means having a central well providing access to said membrane.

4. The device of claim 1, wherein:
   said means for allowing fluid to flow into contact with said membrane is a cap means overlying said membrane, said cap means having a central depression providing access to said membrane; and
   being further provided with a separable sample concentrator, adapted to releasably fit onto said cap means and adapted to concentrate fluid flow to said portion of said membrane having receptor bound thereto.

5. The device of claim 1, wherein said granular absorbent is packed within said body member.

6. The device of claim 1, wherein said granular absorbent is principally composed of silica.

7. The device of claim 1, wherein said granular absorbent is principally composed of calcium chloride.

8. The device of claim 1, wherein said granular absorbent is principally composed of calcium sulfate.

* * * * *